(12) United States Patent
Bonaventura et al.

(10) Patent No.: US 7,074,447 B2
(45) Date of Patent: Jul. 11, 2006

(54) ANTIMICROBIAL COMPOSITION COMPRISING POTASSIUM SORBATE AND LAE

(75) Inventors: Joan Seguer Bonaventura, Barcelona (ES); Sergi Figueras Roca, Barcelona (ES); Joan Bta. Urgell Beltran, Barcelona (ES)

(73) Assignee: Laboratories Miret, S.A., Barcelona (ES)

(*) Notice: Subject to any disclaimer, the term of this patent is extended or adjusted under 35 U.S.C. 154(b) by 187 days.

(21) Appl. No.: 10/475,544

(22) PCT Filed: Apr. 28, 2001

(86) PCT No.: PCT/EP01/04807

§ 371 (c)(1),
(2), (4) Date: Oct. 21, 2003

(87) PCT Pub. No.: WO02/087328

PCT Pub. Date: Nov. 7, 2002

(65) Prior Publication Data

US 2004/0122095 A1 Jun. 24, 2004

(51) Int. Cl.
*A23L 3/34* (2006.01)
*A23L 3/3409* (2006.01)

(52) U.S. Cl. .......... 426/321; 426/330; 426/330.1; 426/330.2; 426/330.3; 426/330.5; 426/303; 426/302; 426/310; 426/334; 426/331

(58) Field of Classification Search ......... 426/321, 426/302, 303, 310, 331, 334, 330, 330.1, 426/330.2, 330.3, 330.5
See application file for complete search history.

(56) References Cited

U.S. PATENT DOCUMENTS

| | | | |
|---|---|---|---|
| 3,825,560 A * | 7/1974 | Saito et al. ............ 548/534 |
| 6,423,354 B1 * | 7/2002 | Monte .................. 426/72 |
| 2001/0046538 A1 * | 11/2001 | Bunger et al. .......... 426/335 |

* cited by examiner

*Primary Examiner*—Milton I. Cano
*Assistant Examiner*—Adepeju O. Pearse
(74) *Attorney, Agent, or Firm*—Schweitzer Cornman Gross & Bondell LLP

(57) ABSTRACT

The invention relates to a novel composition with antimicrobial activity. It is in the food industry a well-known method to use the product L-arginine, Na-lauroyl-ethylester monohydrochloride (LAE). This product is well tolerated and suitable for use in the preservation of all perishable food products. The action of LAE can be further improved by combining the product with a second component selected from the group consisting of potassium sorbate, sodium sorbate and sorbic acid. The weight ratio of LAE to the second component is preferably in the range of 1:50 to 50:1. The combination of the two products leads to a synergistic combined activity against such microorganisms as *Bacillus subtilis, Staphylococcus aureus, Bacillus megaterium, Citrobacter intermedium, Enterobacter aerogenes, Escherichia coli, Candida albicans, Penicillium camemberti* and *Cladosporium cladosporioides*.

15 Claims, No Drawings

ANTIMICROBIAL COMPOSITION COMPRISING POTASSIUM SORBATE AND LAE

The invention relates to a novel composition with antimicrobial activity.

The food industry needs the application of antimicrobial products to warrant the needed storage capability of the produced food-stuff.

A well-known product used in the food industry is LAE (L-arginine, $N^{\alpha}$-lauroyl-ethylester monohydrochloride). The preparation of this product has been described in Spanish patent application ES-A-512643, an improved method in European patent application 95 911 345.7.

LAE is very suitable to be used in the preservation of all perishable food products. Furthermore the product can be used in cosmetic preparations.

LAE has displayed an activity against the following microorganisms:

Gram-Positive Bacteria
*Arthrobacter oxydans* ATCC 8010
*Bacillus cereus* var *mycoide* ATCC 11778
*Bacillus subtilis* ATCC 6633
*Bacillus megaterium* CECT 44
*Clostridium perfringens* ATCC 77454
*Clostridium perfringens* CECT 486
*Listeria monocytogenes* ATCC 7644
*Staphylococcus aureus* ATCC 6538
*Micrococcus luteus* ATCC 9631
*Lactobacillus delbrueckii* ssp *lactis* CECT 372

Gram-Negative Bacteria
*Alcaligenes faecalis* ATCC 8750
*Bordetella bronchiseptica* ATCC 4617
*Citrobacter freundii* ATCC 22636
*Citrobacter intermedium* CECT 401
*Enterobacter aerogenes* CECT 689
*Escherichia coli* ATCC 8739
*Escherichia coli* 0157H7
*Klebsiella pneumoniae* var *pneumoniae* CECT 178
*Proteus mirabilis* CECT 170
*Pseudomonas aeruginosa* ATCC 9027
*Salmonella typhimurium* ATCC16028
*Serratia marcenses* CECT 274
*Mycobacterium phlei* ATCC 41423

Moulds and Yeasts
*Aspergillus niger* ATCC14604
*Aureobasidium pullulans* ATCC 9348
*Cladosporium cladosporioides* ATCC 16022
*Gliocadium virens* ATCC 4645
*Chaetonium globosum* ATCC 6205
*Penicillium chrysogenum* CECT 2802
*Penicillium funiculosum* CECT 2914
*Penicillium camemberti* CECT 2267
*Candida albicans* ATCC 10231
*Rhodotorula rubra* CECT 1158
*Saccharomyces cerevisiae* ATCC 9763

A further product which is used for the preservation of food products is potassium sorbate. This product is regularly used for the preservation of food products, inter alia of food products from the meat industry.

Interaction by different products in a composition directed at the inhibition of growth of microorganisms is for instance described in Spanish patent application ES-A-2124479 3, and European patent applications EP-A-0 900 525 and EP-A-0 980 648.

It was the object of the present application to improve the antimicrobial activity of LAE as a preservative in food products. The improved activity may be reflected by a reduced amount of the product added to the food product to be preserved or to an improved specificity. In general two components in a composition may interact by antagonism, addition (constituting a lack of interaction) and synergism. Synergism is the case when the resulting effect of the combination is significantly greater than the sum of the single effects by each of the components alone.

This object is solved by a combination of LAE with potassium sorbate. Instead of originally using LAE alone, it turned out that a combination of LAE with potassium sorbate led to a surprising change of the antimicrobial activity.

Instead of potassium sorbate the same object is reached by a combination of LAE with calcium sorbate and sorbic acid.

The preferred relative amounts of LAE and potassium sorbate are kept in the range: 1:50 to 50:1. The precise optimum ratio may depend on the pH of the solution. The treatment is usually performed at pH values of 5 or 7.4. The optimum ratio at pH 5 must not necessarily be the same at pH 7.4. Hereafter a number of examples are provided which prove, that the combination is active against a number of different microorganisms at pH 5 as well as at pH 7.4. If for some reason it would be required to perform the treatment at a pH value which is neither pH 5 or pH 7.4 it may be required to perform a control experiment to check the optimum ration at this different pH.

As will be evident hereafter, the action of the combination of the two products is different depending on the type of micro-organism.

The combination of LAE with sorbate is preferably offered as a combination of the dry products. It is preferred to dissolve the combination directly before use in one of the following preferred solvents: water, ethanol, isopropyl alcohol, propylene glycol or another kind of glycol. If the treatment shall be performed at a specific pH value the use of a corresponding buffer solution may be recommendable.

The antimicrobial composition optionally comprises auxiliary components and excipients. Such auxiliary components and excipients can be thickening agents, anti-foam agents, products to obtain the optimal pH value, aroma products, and colouring agents. It is preferred, that the antimicrobial composition comprises LAE and sorbate each in an amount of from 0.01% to 20% by weight relative to the whole weight of the antimicrobial composition.

It is particularly preferred to use the inventive composition for the preservation of meat products, like for instance meat, poultry products, fish, crustaceans, vegetables, greens, emulsions, sauces, confectionery, bakery, dairy products, egg-based products, jams, jellies, beverages, juices, wines, beers, etc.

More in particular the intended use relates to: wine-based flavoured drinks including products covered by regulation (EEC) N° 1601/91; non-alcoholic flavoured drinks; liquid tea concentrates and liquid fruit and herbal infusion concentrates; grape juice, unfermented, for sacramental use; wines as referred to in Regulation (EEC) N° 822/87, alcohol-free wine, fruit wine (including alcohol-free), made wine, cider and perry (including alcohol-free); sod, saft; mead; spirits with less than 15% alcohol by volume; fillings of ravioli and similar products, low-sugars jams, jellies, marmelades and similar low calorie or sugar-free products and other fruit based spreads, marmelades; candied, crystallized and glacé fruit and vegetables; dried fruit, Frugtgrod and Rote Grütze, fruit and vegetable preparation including fruit-based sauces, excluding purée; mousse, compote; salads, and similar products, canned or bottled; vegetables in vinegar, brine or oil (excluding olives); potato dough and pre-fried potato slices; gnocchi; polenta; olives and olive-based preparations; jelly coating of meat products (cooked, cured or dried); paté; surface treatment of dried meat products; semi-preserved fish products including fish roe products, salted, dried fish, shrimps, cooked, *Crangon crangon* and *Crangon vulgaris* cooked; cheese, pre-packed, sliced, unripened cheese, processed cheese, layered cheese and cheese with added foodstuffs; superficial treatment of cheese; cheese substitute, meat substitute, fish substitute, crusteacean substitute; non-heat-treated dairy-based desserts, curdled milk; liquid egg (white, yolk or whole egg), dehydrated, concentrated, frozen and deep-frozen egg products; pre-packed sliced bread and rye-bread; partially baked, pre-packed bakery wares intended for retail sale, fine bakery wares with a water activity of more than 0.65; cereal- or potato-based snacks and coated nuts; batters, confectionery (excluding chocolate), chewing gum; toppings (syrups for pancakes, flavoured syrups for milkshakes and ice cream, similar products), fat emulsions (excluding butter), emulsified sauces, non-emulsified sauces; prepared salads, mustard, seasonings and condiments; liquid soups and broths (excluding canned ones); aspic, liquid dietary food supplements; dietetic foods intended for special medical purposes excluding foods for infants and young children as referred to in Directive 89/398/ECC('); dietetic formulae for weight control intended to replace total daily food intake or an individual meal.

The inventive composition may be added in its final combined form to the product to be preserved or it may be added separately, whereby both single components may be added as dry products to the product to be preserved, or one of the products may be added in the form of a solution or dispersion and the other product as a dry product or both components are added separately as a solvent or a dispersion whereby the solvent or dispersing agent used for each of the two components may be different. For instance LAE may be added as a solution in propylene glycol and potassium sorbate may be added as a solution in propylene glycol as well. It is further possible to add one of the components first and the second of the components in a number of separate steps, which would have the advantage of treating the food product with at least two different ratios of LAE and potassium sorbate which may be of advantage since not all bacteria and other microbes display the same sensitivity against the inventive composition, meaning that the optimum ratio of LAE to potassium sorbate for the treatment against a microorganism A is different from the optimum ratio for the treatment against another microorganism B. The stepwise addition would allow the subsequent activity against different strains.

A number of different embodiments of the invention are illustrated by the following examples.

EXAMPLES

The invention is now explained by a number of examples. In these examples LAE and sorbate alone and in a number of different combinations have been investigated against a number of bacterial preparations. For the analysis usually an internal method was used. Conditions and medium were Mueller Hinton broth (pH 7.4) or (pH 5.0) for bacteria, Sabouraud broth (pH 5.8) for yeast and Sabouraud medium for moulds.

Example 1

In this example the influence of the synergism of combinations of LAE and potassium sorbate in the inventive composition has been investigated.

For that purpose propylene glycol solutions with different concentrations of LAE and potassium sorbate were prepared. LAE (reference 2625) was produced by Lamirsa, Les Fonts de Terrassa, potassium sorbate (reference 7311) was purchased from NUTRINOVA, citric acid (reference 11798) purchased from JUNGBUNZLAUER, and propylene glycol (reference 13679) was purchased from THE DOW CHEMICAL COMPANY. The effects of these preparations were investigated against *Bacillus subtilis* (CECT 356) at pH 7.4.

In the next table 1 the effect of LAE and potassium sorbate is displayed when administered alone and in combination. The table indicates the concentrations of the ingredients used, whereby a value for LAE/S of 4%/10% means that the final preparation contained LAE at a concentration of 4% (w/w) and potassium sorbate at a concentration of 10% (w/w).

The interaction of the two components of the antimicrobial mixture is calculated according to the method described by Kull et al. (Kull F. C., Eisman P. C., Sylwestrowicz H. D. and Mayer R. L., Applied Microbiology, 1961; 6:538–541). According to this method the so-called synergy index is calculated according to the following formula:

Synergy index $SI = Q_{lae}/Q_{LAE} + Q_s/Q_S$.

The elements used for the calculation of the synergy index according to the above formula have the following meaning:

$Q_{lae}$=minimum inhibition concentration of LAE in the mixture of LAE and potassium sorbate, $Q_{LAE}$=minimum inhibition concentration of LAE as single antimicrobial without potassium sorbate, $Q_s$=minimum inhibition concentration of potassum sorbate in the mixture of LAE and potassium sorbate and $Q_S$=minimum inhibition concentration of potassium sorbate as single antimicrobial without LAE.

All indicated symbols indicate a particular concentration leading to a particular end point, in this case the inhibition of growth of *Bacillus subtilis*, so that the selected end point is in fact the minimal inhibitory concentration (mic).

The method of Kull et al. for the calculation of the synergy index allows a very quick evaluation of the type of interaction displayed by the two components of the antimicrobial mixture. When the synergy index displays a value of more than 1, then there is an antagonism between the two components. When the synergy index is 1, then there is an addition of the effects of the two components. When the synergy index displays a value of less than 1, then there is a synergism between the two components.

TABLE 1

| LAE/S | LAE/sorbate | Qlae | QLAE | Qlae/QLAE | Qs | QS | Qs/QS | SI |
|---|---|---|---|---|---|---|---|---|
| 4%/10% | 0.40 | 6.8 | 12.8 | 0.53 | 17 | 1024 | 0.02 | 0.55 |
| 5%/10% | 0.50 | 12.8 | 12.8 | 1.0 | 25.6 | 1024 | 0.03 | 1.03 |
| 6%/8% | 0.75 | 10.2 | 12.8 | 0.80 | 13.6 | 1024 | 0.01 | 0.81 |
| 5%/5% | 1.00 | 8.5 | 12.8 | 0.66 | 8.5 | 1024 | 0.01 | 0.67 |
| 8%/6% | 1.33 | 5.12 | 12.8 | 0.40 | 3.84 | 1024 | 0.00 | 0.40 |
| 10%/5% | 2.00 | 12.8 | 12.8 | 1.00 | 6.4 | 1024 | 0.01 | 1.01 |
| 10%/3.75% | 2.67 | 12.8 | 12.8 | 1.00 | 4.8 | 1024 | 0.00 | 1.00 |
| 20%/0% | — | 12.8 | 12.8 | 1.00 | 0 | 1024 | 0.00 | 1.00 |
| 0%/20% | — | 0 | 12.8 | 0 | 1024 | 1024 | 1.00 | 1.00 |

It is evident from the data in the table-1, that the most optimal combination of the two components LAE and potassium sorbate is found at a concentration of 8% (w/w) LAE and 6% (w/w) potassium sorbate.

Example 2

A further investigation against the same microorganism as in example 1 was performed using the pH value of 5.0 instead of 7.4 and slightly extending the concentration range.

In the next table 2 the effect of LAE and potassium sorbate is displayed when administered alone and in combination. The table indicates the concentrations of the ingredients used, whereby a value for LAE/S of 1%/9% means that the final preparation contained LAE at a concentration of 1% (w/w) and potassium sorbate at a concentration of 9% (w/w).

TABLE 2

| LAE/S | LAE/sorbate | Qlae | QLAE | Qlae/QLAE | Qs | QS | Qs/QS | SI |
|---|---|---|---|---|---|---|---|---|
| 1%/9% | 0.11 | 10.24 | 29.3 | 0.35 | 92.16 | 1024 | 0.09 | 0.44 |
| 2%/8% | 0.25 | 16.38 | 29.3 | 0.56 | 65.52 | 1024 | 0.06 | 0.62 |
| 3%/7% | 0.43 | 17.55 | 29.3 | 0.60 | 40.95 | 1024 | 0.04 | 0.64 |
| 4%/6% | 0.67 | 23.4 | 29.3 | 0.80 | 35.10 | 1024 | 0.03 | 0.83 |
| 5%/5% | 1.00 | 25.6 | 29.3 | 0.87 | 25.60 | 1024 | 0.03 | 0.90 |
| 6%/4% | 1.50 | 30.72 | 29.3 | 1.05 | 20.48 | 1024 | 0.02 | 1.07 |
| 7%/3% | 2.33 | 35.84 | 29.3 | 1.22 | 15.36 | 1024 | 0.02 | 1.24 |
| 8%/2% | 4.00 | 40.96 | 29.3 | 1.40 | 10.24 | 1024 | 0.01 | 1.41 |
| 9%/1% | 9.00 | 19.35 | 29.3 | 0.66 | 2.15 | 1024 | 0.00 | 0.66 |
| 10%/0% | — | 29.3 | 29.3 | 1.00 | 0 | 1024 | 0.00 | 1.00 |
| 0%/10% | — | 0 | 29.3 | 0 | 1024.00 | 1024 | 1.00 | 1.00 |

Example 3

In this example the influence of the synergism of combinations of LAE and potassium sorbate in the inventive composition has been investigated.

For that purpose aqueous solutions with different concentrations of LAE and potassium sorbate were prepared and the effect of these preparations were investigated against *Staphylococcus aureus* (ATCC 6538) at pH 7.4.

In the next table 3 the effect of LAE and potassium is displayed when administered alone and in combination. The table indicates the concentrations of the ingredients used, whereby a value for LAE/S of 4%/10% means that the final preparation contained LAE at a concentration of 4% (w/w) and potassium sorbate at a concentration of 10% (w/w).

Again the effects of the components alone and in combination have been calculated using the same method as described at Example 1.

TABLE 3

| LAE/S | LAE/sorbate | Qlae | QLAE | Qlae/QLAE | Qs | QS | Qs/QS | SI |
|---|---|---|---|---|---|---|---|---|
| 4%/10% | 0.40 | 2.56 | 3.2 | 0.8 | 6.4 | 1536 | 0.00 | 0.80 |
| 5%/10% | 0.50 | 3.2 | 3.2 | 1.0 | 6.4 | 1536 | 0.00 | 1.00 |
| 6%/8% | 0.75 | 1.92 | 3.2 | 0.60 | 2.56 | 1536 | 0.00 | 0.60 |
| 5%/5% | 1.00 | 3.2 | 3.2 | 1.0 | 3.2 | 1536 | 0.00 | 1.00 |
| 8%/6% | 1.33 | 5.12 | 3.2 | 1.60 | 3.84 | 1536 | 0.00 | 1.60 |
| 10%/5% | 2.00 | 3.2 | 3.2 | 1.0 | 1.6 | 1536 | 0.00 | 1.00 |
| 10%/3.75% | 2.67 | 3.2 | 3.2 | 1.0 | 1.2 | 1536 | 0.00 | 1.00 |
| 20%/0% | — | 3.2 | 3.2 | 1.0 | 0 | 1536 | 0.00 | 1.00 |
| 0%/20% | — | 0 | 3.2 | 0.0 | 1536 | 1536 | 1.00 | 1.00 |

It is evident from the table-3, that the optimal concentration for the combination of the two components is 6% (w/w) of LAE and 8% (w/w) of potassium sorbate.

Example 4

A further investigation against the same microorganism as in example 3 was performed using the pH value of 5.0 instead of 7.4 and slightly extending the concentration range.

In the next table 4 the effect of LAE and potassium sorbate is displayed when administered alone and in combination. The table indicates the concentrations of the ingredients used, whereby a value for LAE/S of 1%/9% means that the final preparation contained LAE at a concentration of 1% (w/w) and potassium sorbate at a concentration of 9% (w/w).

TABLE 4

| LAE/S | LAE/sorbate | Qlae | QLAE | Qlae/QLAE | Qs | QS | Qs/QS | SI |
|---|---|---|---|---|---|---|---|---|
| 1%/9% | 0.11 | 10.24 | 29.3 | 0.35 | 92.16 | 1024 | 0.09 | 0.44 |
| 2%/8% | 0.25 | 16.38 | 29.3 | 0.56 | 65.52 | 1024 | 0.06 | 0.62 |
| 3%/7% | 0.43 | 20.49 | 29.3 | 0.70 | 47.81 | 1024 | 0.05 | 0.75 |
| 4%/6% | 0.67 | 23.4 | 29.3 | 0.80 | 35.10 | 1024 | 0.03 | 0.83 |
| 5%/5% | 1.00 | 25.6 | 29.3 | 0.87 | 25.60 | 1024 | 0.03 | 0.90 |
| 6%/4% | 1.50 | 28.7 | 29.3 | 1.05 | 20.48 | 1024 | 0.02 | 1.07 |
| 7%/3% | 2.33 | 40.96 | 29.3 | 0.98 | 12.3 | 1024 | 0.01 | 0.99 |
| 8%/2% | 4.00 | 19.35 | 29.3 | 1.40 | 10.24 | 1024 | 0.01 | 1.41 |
| 9%/1% | 9.00 | 19.35 | 29.3 | 0.66 | 2.15 | 1024 | 0.00 | 0.66 |
| 10%/0% | — | 29.3 | 29.3 | 1.00 | 0 | 1024 | 0.00 | 1.00 |
| 0%/10% | — | 0 | 29.3 | 0 | 1024.00 | 1024 | 1.00 | 1.00 |

Example 5

In this example the influence of the synergism of combinations of LAE and potassium sorbate in the inventive composition has been investigated.

For that purpose aqueous solutions with different concentrations of LAE and potassium sorbate were prepared and the effect of these preparations were investigated against *Bacillus megaterium* (CECT 44) at pH 7.4.

In the next table 5 the effect of LAE and potassium is displayed when administered alone and in combination. The table indicates the concentrations of the ingredients used, whereby a value for LAE/S of 4%/10% means that the final preparation contained LAE at a concentration of 4% (w/w) and potassium sorbate at a concentration of 10% (w/w).

Again the effects of the components alone and in combination have been calculated using the same method as described at Example 1.

TABLE 5

| LAE/S | LAE/sorbate | Qlae | QLAE | Qlae/QLAE | Qs | QS | Qs/QS | SI |
|---|---|---|---|---|---|---|---|---|
| 4%/10% | 0.40 | 5.12 | 6.4 | 0.8 | 12.8 | 1024 | 0.01 | 0.81 |
| 5%/10% | 0.50 | 6.4 | 6.4 | 1 | 102.4 | 1024 | 0.10 | 1.10 |
| 6%/8% | 0.75 | 3.84 | 6.4 | 0.6 | 5.12 | 1024 | 0.01 | 0.61 |
| 5%/5% | 1.00 | 6.4 | 6.4 | 1 | 6.4 | 1024 | 0.01 | 1.01 |
| 8%/6% | 1.33 | 10.24 | 6.4 | 1.6 | 7.68 | 1024 | 0.01 | 1.61 |
| 10%/5% | 2.00 | 6.4 | 6.4 | 1 | 3.2 | 1024 | 0.00 | 1.00 |
| 10%/3.75% | 2.67 | 6.4 | 6.4 | 1 | 2.4 | 1024 | 0.00 | 1.00 |
| 20%/0% | — | 6.4 | 6.4 | 1 | 0 | 1024 | 0.00 | 1.00 |
| 0%/20% | — | 0 | 6.4 | 0 | 1024 | 1024 | 1.00 | 1.00 |

The data of the table-5 prove, that a combination of 6% (w/w) LAE with 8% (w/w) potassium sorbate leads to an optimum result concerning the inhibition of growth of *Bacillus megaterium*.

Example 6

In this example the influence of the synergism of combinations of LAE and potassium sorbate in the inventive composition has been investigated.

For that purpose aqueous solutions with different concentrations of LAE and potassium sorbate were prepared and the effect of these preparations were investigated against *Citrobacter intermedium* (CECT 401).

The same method was used as described for example 1.

In the next table 6 the effect of LAE and potassium is displayed when administered alone and in combination. The table indicates the concentrations of the ingredients used, whereby a value for LAE/S of 4%/10% means that the final preparation contained LAE at a concentration of 4% (w/w) and potassium sorbate at a concentration of 10% (w/w).

Again the effects of the components alone and in combination have been calculated using the same method as described at Example 1.

TABLE 6

| LAE/S | LAE/sorbate | Qlae | QLAE | Qlae/QLAE | Qs | QS | Qs/QS | SI |
|---|---|---|---|---|---|---|---|---|
| 4%/10% | 0.40 | 40.95 | 25.6 | 1.60 | 102.40 | 1536 | 0.07 | 1.67 |
| 5%/10% | 0.50 | 51.2 | 25.6 | 2.00 | 12.80 | 1536 | 0.01 | 2.01 |
| 6%/8% | 0.75 | 20.46 | 25.6 | 0.80 | 27.28 | 1536 | 0.02 | 0.82 |
| 5%/5% | 1.00 | 38.4 | 25.6 | 1.50 | 38.40 | 1536 | 0.03 | 1.53 |
| 8%/6% | 1.33 | 40.95 | 25.6 | 1.60 | 30.72 | 1536 | 0.02 | 1.62 |
| 10%/5% | 2.00 | 51.2 | 25.6 | 2.00 | 25.60 | 1536 | 0.02 | 2.02 |
| 10%/3.75% | 2.67 | 34.1 | 25.6 | 1.33 | 12.79 | 1536 | 0.01 | 1.34 |
| 20%/0% | — | 25.6 | 25.6 | 1.00 | 0 | 1536 | 0.00 | 1.00 |
| 0%/20% | — | 0 | 25.6 | 0 | 1536 | 1536 | 1.00 | 1.00 |

The data of the table-6 prove, that a combination of 6% (w/w) LAE with 8% (w/w) potassium sorbate leads to an optimum result concerning the inhibition of growth of *Citrobacter intermedium*.

Example 7

A further investigation against the same microorganism as in example 6 was performed using the pH value of 5.0 instead of 7.4 and slightly extending the concentration range.

In the next table 7 the effect of LAE and potassium sorbate is displayed when administered alone and in combination. The table indicates the concentrations of the ingredients used, whereby a value for LAE/S of 1%/9% means that the final preparation contained LAE at a concentration of 1% (w/w) and potassium sorbate at a concentration of 9% (w/w).

TABLE 7

| LAE/S | LAE/sorbate | Qlae | QLAE | Qlae/QLAE | Qs | QS | Qs/QS | SI |
|---|---|---|---|---|---|---|---|---|
| 1%/9% | 0.11 | 5.12 | 12.8 | 0.40 | 46.08 | 512 | 0.09 | 0.49 |
| 2%/8% | 0.25 | 10.24 | 12.8 | 0.80 | 40.96 | 512 | 0.08 | 0.88 |
| 3%/7% | 0.43 | 8.79 | 12.8 | 0.69 | 20.51 | 512 | 0.04 | 0.73 |
| 4%/6% | 0.67 | 8.6 | 12.8 | 0.67 | 12.9 | 512 | 0.03 | 0.70 |
| 5%/5% | 1.00 | 12.8 | 12.8 | 1.00 | 12.8 | 512 | 0.03 | 1.03 |
| 6%/4% | 1.50 | 17.58 | 12.8 | 1.37 | 11.72 | 512 | 0.02 | 1.40 |
| 7%/3% | 2.33 | 13.44 | 12.8 | 1.05 | 5.76 | 512 | 0.01 | 1.06 |
| 8%/2% | 4.00 | 15.36 | 12.8 | 1.20 | 3.84 | 512 | 0.01 | 1.21 |
| 9%/1% | 9.00 | 15.39 | 12.8 | 1.20 | 1.71 | 512 | 0.00 | 1.21 |
| 10%/0% | — | 12.8 | 12.8 | 1.00 | 0 | 512 | 0.00 | 1.00 |
| 0%/10% | — | 0 | 12.8 | 0 | 1024.00 | 512 | 1.00 | 1.00 |

In this example the influence of the synergism of combinations of LAE and potassium sorbate in the inventive composition has been investigated.

For that purpose aqueous solutions with different concentrations of LAE and potassium sorbate were prepared and the effect of these preparations were investigated against *Enterobacter aerogenes* (ATCC 13048) at pH 7.4.

The same method was used as described for example 1.

In the next table 8 the effect of LAE and potassium is displayed when administered alone and in combination. The table indicates the concentrations of the ingredients used, whereby a value for LAE/S of 4%/10% means that the final preparation contained LAE at a concentration of 4% (w/w) and potassium sorbate at a concentration of 10% (w/w).

Again the effects of the components alone and in combination have been calculated using the same method as described at Example 1.

TABLE 8

| LAE/S | LAE/sorbate | Qlae | Qlae/QLAE | QLAE | Qs | QS | Qs/QS | SI |
|---|---|---|---|---|---|---|---|---|
| 4%/10% | 0.40 | 30.72 | 68.2 | 0.45 | 76.8 | 1536 | 0.05 | 0.50 |
| 5%/10% | 0.50 | 51.2 | 68.2 | 0.75 | 102.4 | 1536 | 0.07 | 0.82 |
| 6%/8% | 0.75 | 61.44 | 68.2 | 0.90 | 81.92 | 1536 | 0.05 | 0.95 |
| 5%/5% | 1.00 | 51.2 | 68.2 | 0.75 | 51.2 | 1536 | 0.03 | 0.78 |
| 8%/6% | 1.33 | 81.92 | 68.2 | 1.20 | 61.44 | 1536 | 0.04 | 1.24 |
| 10%/5% | 2.00 | 102.4 | 68.2 | 1.50 | 51.2 | 1536 | 0.03 | 1.53 |
| 10%/3.75% | 2.67 | 76.8 | 68.2 | 1.13 | 28.8 | 1536 | 0.02 | 1.14 |
| 20%/0% | — | 68.2 | 68.2 | 1.00 | 0 | 1536 | 0.00 | 1.00 |
| 0%/20% | — | 0 | 68.2 | 0 | 1536 | 1536 | 1.00 | 1.00 |

The data of the table-8 prove, that a combination of 4% (w/w) of LAE with 10% (w/w) potassium sorbate leads to an optimum result concerning the inhibition of growth of *Enterobacter aerogenes*.

Example 9

A further investigation against the same microorganism as in example 8 was performed using the pH value of 5.0 instead of 7.4 and slightly extending the concentration range.

In the next table 9 the effect of LAE and potassium sorbate is displayed when administered alone and in combination. The table indicates the concentrations of the ingredients used, meaning that a value for LAE/S of 1%/9% means that the final preparation contained LAE at a concentration of 1% (w/w) and potassium sorbate at a concentration of 9% (w/w).

TABLE 9

| LAE/S | LAE/sorbate | Qlae | QLAE | Qlae/QLAE | Qs | QS | Qs/QS | SI |
|---|---|---|---|---|---|---|---|---|
| 1%/9% | 0.11 | 10.24 | 21.5 | 0.48 | 92.16 | 1024 | 0.09 | 0.57 |
| 2%/8% | 0.25 | 10.24 | 21.5 | 0.48 | 40.96 | 1024 | 0.04 | 0.52 |
| 3%/7% | 0.43 | 12.3 | 21.5 | 0.57 | 28.7 | 1024 | 0.03 | 0.60 |
| 4%/6% | 0.67 | 23.4 | 21.5 | 1.09 | 35.10 | 1024 | 0.03 | 1.12 |
| 5%/5% | 1.00 | 17.05 | 21.5 | 0.79 | 17.05 | 1024 | 0.02 | 0.81 |
| 6%/4% | 1.50 | 30.72 | 21.5 | 1.43 | 20.48 | 1024 | 0.02 | 1.45 |
| 7%/3% | 2.33 | 20.51 | 21.5 | 0.95 | 8.79 | 1024 | 0.01 | 0.96 |
| 8%/2% | 4.00 | 32.8 | 21.5 | 1.53 | 8.2 | 1024 | 0.01 | 1.53 |
| 9%/1% | 9.00 | 19.35 | 21.5 | 0.90 | 2.15 | 1024 | 0.00 | 0.90 |
| 10%/0% | — | 21.5 | 21.5 | 1.00 | 0 | 1024 | 0.00 | 1.00 |
| 0%/10% | — | 0 | 21.5 | 0 | 1024.00 | 1024 | 1.00 | 1.00 |

Example 10

In this example the influence of the synergism of combinations of LAE and potassium sorbate in the inventive composition has been investigated.

For that purpose aqueous solutions with different concentrations of LAE and potassium sorbate were prepared and the effect of these preparations were investigated against *Escherichia coli* (ATCC 8739).

The same method was used as described for example 1.

In the next table 10 the effect of LAE and potassium is displayed when administered alone and in combination. The table indicates the concentrations of the ingredients used, whereby a value for LAE/S of 4%/10% means that the final preparation contained LAE at a concentration of 4% (w/w) and potassium sorbate at a concentration of 10% (w/w).

Again the effects of the components alone and in combination have been calculated using the same method as described at Example 1.

Example 8

TABLE 10

| LAE/S | LAE/Sorbate | Qlae | QLAE | Qlae/QLAE | Qs | QS | Qs/QS | SI |
|---|---|---|---|---|---|---|---|---|
| 4%/10% | 0.40 | 30.72 | 25.6 | 1.20 | 76.8 | 1536 | 0.05 | 1.25 |
| 5%/10% | 0.50 | 51.2 | 25.6 | 2.00 | 102.4 | 1536 | 0.07 | 2.07 |
| 6%/8% | 0.75 | 20.46 | 25.6 | 0.80 | 81.92 | 1536 | 0.05 | 0.85 |
| 5%/5% | 1.00 | 25.6 | 25.6 | 1.00 | 51.2 | 1536 | 0.03 | 1.03 |
| 8%/6% | 1.33 | 27.28 | 25.6 | 1.07 | 61.44 | 1536 | 0.04 | 1.11 |
| 10%/5% | 2.00 | 34.1 | 25.6 | 1.33 | 51.2 | 1536 | 0.03 | 1.37 |
| 10%/3.75% | 2.67 | 34.1 | 25.6 | 1.33 | 28.8 | 1536 | 0.02 | 1.35 |
| 20%/0% | — | 25.6 | 25.6 | 1.00 | 0 | 1536 | 0.00 | 1.00 |
| 0%/20% | — | 0 | 25.6 | 0 | 1536 | 1536 | 1.00 | 1.00 |

The data of the table-10 prove, that a combination of 6% (w/w) of LAE with 8% (w/w) potassium sorbate leads to an optimum result concerning the inhibition of growth of *Escherichia coli*.

Example 11

A further investigation against the same microorganism as in example 10 was performed using the pH value of 5.0 instead of 7.4 and slightly extending the concentration range.

In the next table 11 the effect of LAE and potassium sorbate is displayed when administered alone and in combination. The table indicates the concentrations of the ingredients used, whereby a value for LAE/S of 1%/9% means that the final preparation contained LAE at a concentration of 1% (w/w) and potassium sorbate at a concentration of 9% (w/w).

TABLE 11

| LAE/S | LAE/sorbate | Qlae | QLAE | Qlae/QLAE | Qs | QS | Qs/QS | SI |
|---|---|---|---|---|---|---|---|---|
| 1%/9% | 0.11 | 10.24 | 21.5 | 0.48 | 92.16 | 1024 | 0.09 | 0.57 |
| 2%/8% | 0.25 | 10.24 | 21.5 | 0.48 | 40.96 | 1024 | 0.04 | 0.52 |
| 3%/7% | 0.43 | 12.3 | 21.5 | 0.57 | 28.7 | 1024 | 0.03 | 0.60 |
| 4%/6% | 0.67 | 23.4 | 21.5 | 1.09 | 35.10 | 1024 | 0.03 | 1.12 |
| 5%/5% | 1.00 | 17.05 | 21.5 | 0.79 | 17.05 | 1024 | 0.02 | 0.81 |
| 6%/4% | 1.50 | 30.72 | 21.5 | 1.43 | 20.48 | 1024 | 0.02 | 1.45 |
| 7%/3% | 2.33 | 20.51 | 21.5 | 0.95 | 8.79 | 1024 | 0.01 | 0.96 |
| 8%/2% | 4.00 | 27.28 | 21.5 | 1.27 | 6.82 | 1024 | 0.01 | 1.28 |
| 9%/1% | 9.00 | 19.35 | 21.5 | 0.90 | 2.15 | 1024 | 0.00 | 0.90 |
| 10%/0% | — | 21.5 | 21.5 | 1.00 | 0 | 1024 | 0.00 | 1.00 |
| 0%/10% | — | 0 | 21.5 | 0 | 1024.00 | 1024 | 1.00 | 1.00 |

Example 12

In this example the influence of the synergism of combinations of LAE and potassium sorbate in the inventive composition has been investigated.

For that purpose aqueous solutions with different concentrations of LAE and potassium sorbate were prepared and the effect of these preparations were investigated against *Candida albicans* (ATCC 10231) at pH 7.4.

The same method was used as described for example 1.

In the next table 12 the effect of LAE and potassium is displayed when administered alone and in combination. The table indicates the concentrations of the ingredients used, whereby a value for LAE/S of 4%/10% means that the final preparation contained LAE at a concentration of 4% (w/w) and potassium sorbate at a concentration of 10% (w/w).

Again the effects of the components alone and in combination have been calculated using the same method as described at Example 1.

TABLE 12

| LAE/S | LAE/Sorbate | Qlae | QLAE | Qlae/QLAE | Qs | QS | Qs/QS | SI |
|---|---|---|---|---|---|---|---|---|
| 4%/10% | 0.40 | 20.48 | 25.60 | 0.80 | 51.20 | 1024 | 0.05 | 0.85 |
| 5%/10% | 0.50 | 51.20 | 25.60 | 2.00 | 102.4 | 1024 | 0.10 | 2.10 |
| 6%/8% | 0.75 | 15.36 | 25.60 | 0.60 | 20.48 | 1024 | 0.02 | 0.62 |
| 5%/5% | 1.00 | 25.60 | 25.60 | 1.00 | 25.60 | 1024 | 0.03 | 1.03 |
| 8%/6% | 1.33 | 40.96 | 25.60 | 1.60 | 30.72 | 1024 | 0.03 | 1.63 |
| 10%/5% | 2.00 | 25.60 | 25.60 | 1.00 | 12.80 | 1024 | 0.01 | 1.01 |
| 10%/3.75% | 2.67 | 34.10 | 25.60 | 1.33 | 12.79 | 1024 | 0.01 | 1.34 |
| 20%/0% | — | 25.60 | 25.60 | 1.00 | 0.00 | 1024 | 0.00 | 1.00 |
| 0%/20% | — | 0 | 25.60 | 0 | 1024.00 | 1024 | 1.00 | 1.00 |

The data of the table-12 prove, that a combination of 6% (w/w) of LAE with 8% (w/w) potassium sorbate leads to an optimum result concerning the inhibition of growth of *Candida albicans*.

Example 13

A further investigation against the same microorganism as in example 12 was performed using the pH value of 5.0 instead of 7.4 and slightly extending the concentration range.

In the next table 13 the effect of LAE and potassium sorbate is displayed when administered alone and in combination. The table indicates the concentrations of the ingredients used, whereby a value for LAE/S of 1%/9% means that the final preparation contained LAE at a concentration of 1% (w/w) and potassium sorbate at a concentration of 9% (w/w).

TABLE 13

| LAE/S | LAE/sorbate | Qlae | QLAE | Qlae/QLAE | Qs | QS | Qs/QS | SI |
|---|---|---|---|---|---|---|---|---|
| 1%/9% | 0.11 | 10.24 | 29.3 | 0.35 | 92.16 | 1024 | 0.09 | 0.44 |
| 2%/8% | 0.25 | 13.66 | 29.3 | 0.47 | 54.64 | 1024 | 0.05 | 0.52 |
| 3%/7% | 0.43 | 20.49 | 29.3 | 0.70 | 47.81 | 1024 | 0.05 | 0.75 |
| 4%/6% | 0.67 | 23.4 | 29.3 | 0.80 | 35.10 | 1024 | 0.03 | 0.83 |
| 5%/5% | 1.00 | 20.5 | 29.3 | 0.70 | 20.5 | 1024 | 0.02 | 0.72 |
| 6%/4% | 1.50 | 40.98 | 29.3 | 1.40 | 27.32 | 1024 | 0.03 | 1.43 |
| 7%/3% | 2.33 | 48.7 | 29.3 | 0.98 | 12.3 | 1024 | 0.01 | 0.99 |
| 8%/2% | 4.00 | 27.28 | 29.3 | 0.93 | 6.82 | 1024 | 0.01 | 0.94 |
| 9%/1% | 9.00 | 46.08 | 29.3 | 1.57 | 5.12 | 1024 | 0.01 | 1.58 |
| 10%/0% | — | 29.3 | 29.3 | 1.00 | 0 | 1024 | 0.00 | 1.00 |
| 0%/10% | — | 0 | 29.3 | 0 | 1024.00 | 1024 | 1.00 | 1.00 |

Example 14

In this example the influence of the synergism of combinations of LAE and potassium sorbate in the inventive composition has been investigated.

For that purpose aqueous solutions with different concentrations of LAE and potassium sorbate were prepared and the effect of these preparations were investigated against *Penicillium camemberti* (CECT 2267) at pH 7.4.

The same method was used as described for example 1.

In the next table 14 the effect of LAE and potassium is displayed when administered alone and in combination. The table indicates the concentrations of the ingredients used, whereby a value for LAE/S of 4%/10% means that the final preparation contained LAE at a concentration of 4% (w/w) and potassium sorbate at a concentration of 10% (w/w).

Again the effects of the components alone and in combination have been calculated using the same method as described at Example 1.

TABLE 14

| LAE/S | LAE/Sorbate | Qlae | QLAE | Qlae/QLAE | Qs | QS | Qs/QS | SI |
|---|---|---|---|---|---|---|---|---|
| 4%/10% | 0.40 | 40.96 | 68.2 | 0.60 | 76.8 | 2048 | 0.04 | 0.64 |
| 5%/10% | 0.50 | 51.2 | 68.2 | 0.75 | 102.4 | 2048 | 0.05 | 0.80 |
| 6%/8% | 0.75 | 61.44 | 68.2 | 0.90 | 61.44 | 2048 | 0.03 | 0.93 |
| 5%/5% | 1.00 | 51.2 | 68.2 | 0.75 | 38.4 | 2048 | 0.02 | 0.77 |
| 8%/6% | 1.33 | 81.92 | 68.2 | 1.20 | 30.72 | 2048 | 0.02 | 1.22 |
| 10%/5% | 2.00 | 76.8 | 68.2 | 1.13 | 17.05 | 2048 | 0.01 | 1.13 |
| 10%/3.75% | 2.67 | 76.8 | 68.2 | 1.13 | 19.2 | 2048 | 0.01 | 1.14 |
| 20%/0% | — | 68.2 | 68.2 | 1.00 | 0 | 2048 | 0.00 | 1.00 |
| 0%/20% | — | 0 | 68.2 | 0 | 2048 | 2048 | 1.00 | 1.00 |

The data of the table-14 prove, that a combination of 4% (w/w) of LAE with 10% (w/w) potassium sorbate leads to an optimum result concerning the inhibition of growth of *Penicillium camemberti*.

Example 15

A further investigation against the same microorganism as in example 14 was performed using the pH value of 5.0 instead of 7.4 and slightly extending the concentration range.

In the next table 15 the effect of LAE and potassium sorbate is displayed when administered alone and in combination. The table indicates the concentrations of the ingredients used, whereby a value for LAE/S of 1%/9% means that the final preparation contained LAE at a concentration of 1% (w/w) and potassium sorbate at a concentration of 9% (w/w).

TABLE 15

| LAE/S | LAE/sorbate | Qlae | QLAE | Qlae/QLAE | Qs | QS | Qs/QS | SI |
|---|---|---|---|---|---|---|---|---|
| 1%/9% | 0.11 | 10.24 | 58.5 | 0.18 | 92.16 | 1024 | 0.09 | 0.27 |
| 2%/8% | 0.25 | 20.48 | 58.5 | 0.35 | 81.92 | 1024 | 0.08 | 0.43 |
| 3%/7% | 0.43 | 30.72 | 58.5 | 0.53 | 71.68 | 1024 | 0.07 | 0.60 |
| 4%/6% | 0.67 | 40.96 | 58.5 | 0.70 | 61.44 | 1024 | 0.06 | 0.76 |
| 5%/5% | 1.00 | 51.2 | 58.5 | 0.88 | 51.2 | 1024 | 0.05 | 0.93 |
| 6%/4% | 1.50 | 49.14 | 58.5 | 0.84 | 32.76 | 1024 | 0.03 | 0.87 |
| 7%/3% | 2.33 | 71.68 | 58.5 | 1.23 | 30.72 | 1024 | 0.03 | 1.26 |
| 8%/2% | 4.00 | 81.92 | 58.5 | 1.40 | 20.48 | 1024 | 0.02 | 1.42 |
| 9%/1% | 9.00 | 52.65 | 58.5 | 0.90 | 5.85 | 1024 | 0.01 | 0.91 |
| 10%/0% | — | 58.5 | 58.5 | 1.00 | 0 | 1024 | 0.00 | 1.00 |
| 0%/10% | — | 0 | 58.5 | 0 | 1024.00 | 1024 | 1.00 | 1.00 |

Example 16

In this example the influence of the synergism of combinations of LAE and potassium sorbate in the inventive composition has been investigated.

For that purpose aqueous solutions with different concentrations of LAE and potassium sorbate were prepared and the effect of these preparations were investigated against *Cladosporium cladosporioides* (ATCC 16022).

The same method was used as described for example 1.

In the next table 16 the effect of LAE and potassium is displayed when administered alone and in combination. The table indicates the concentrations of the ingredients used, whereby a value for LAE/S of 4%/10% means that the final preparation contained LAE at a concentration of 4% (w/w) and potassium sorbate at a concentration of 10% (w/w).

Again the effects of the components alone and in combination have been calculated using the same method as described at Example 1.

TABLE 16

| LAE/S | LAE/Sorbate | Qlae | QLAE | Qlae/QLAE | Qs | QS | Qs/QS | SI |
|---|---|---|---|---|---|---|---|---|
| 4%/10% | 0.40 | 13.64 | 25.6 | 0.53 | 34.1 | 1024 | 0.03 | 0.57 |
| 5%/10% | 0.50 | 17.05 | 25.6 | 0.67 | 34.1 | 1024 | 0.03 | 0.70 |
| 6%/8% | 0.75 | 15.36 | 25.6 | 0.60 | 20.48 | 1024 | 0.02 | 0.62 |
| 5%/5% | 1.00 | 12.8 | 25.6 | 0.50 | 12.8 | 1024 | 0.01 | 0.51 |
| 8%/6% | 1.33 | 27.28 | 25.6 | 1.07 | 20.46 | 1024 | 0.02 | 1.09 |
| 10%/5% | 2.00 | 34.1 | 25.6 | 1.33 | 17.05 | 1024 | 0.02 | 1.35 |
| 10%/3.75% | 2.67 | 34.1 | 25.6 | 1.33 | 0 | 1024 | 0.00 | 1.33 |
| 20%/0% | — | 25.6 | 25.6 | 1.00 | 0 | 1024 | 0.00 | 1.00 |
| 0%/20% | — | 0 | 25.6 | 0.00 | 1024 | 1024 | 1.00 | 1.00 |

The data of the table-16 prove, that a combination of 5% (w/w) of LAE with 5% (w/w) potassium sorbate leads to an optimum result concerning the inhibition of growth of *Cladosporium cladosporioides*.

Example 17

A further investigation against the same microorganism as in example 16 was performed using the pH value of 5.0 instead of 7.4 and slightly extending the concentration range.

In the next table 17 the effect of LAE and potassium sorbate is displayed when administered alone and in combination. The table indicates the concentrations of the ingredients used, whereby a value for LAE/S of 1%/9% means that the final preparation contained LAE at a concentration of 1% (w/w) and potassium sorbate at a concentration of 9% (w/w).

TABLE 17

| LAE/S | LAE/sorbate | Qlae | QLAE | Qlae/QLAE | Qs | QS | Qs/QS | SI |
|---|---|---|---|---|---|---|---|---|
| 1%/9% | 0.11 | 10.24 | 58.5 | 0.18 | 92.16 | 1024 | 0.09 | 0.27 |
| 2%/8% | 0.25 | 20.48 | 58.5 | 0.35 | 81.92 | 1024 | 0.08 | 0.43 |
| 3%/7% | 0.43 | 30.72 | 58.5 | 0.53 | 71.68 | 1024 | 0.07 | 0.60 |
| 4%/6% | 0.67 | 40.96 | 58.5 | 0.70 | 61.44 | 1024 | 0.06 | 0.76 |
| 5%/5% | 1.00 | 51.2 | 58.5 | 0.88 | 51.2 | 1024 | 0.05 | 0.93 |
| 6%/4% | 1.50 | 61.44 | 58.5 | 1.05 | 40.96 | 1024 | 0.04 | 1.09 |
| 7%/3% | 2.33 | 71.68 | 58.5 | 1.23 | 30.72 | 1024 | 0.03 | 1.26 |
| 8%/2% | 4.00 | 81.92 | 58.5 | 1.40 | 20.48 | 1024 | 0.02 | 1.42 |
| 9%/1% | 9.00 | 61.47 | 58.5 | 1.05 | 6.83 | 1024 | 0.01 | 1.06 |
| 10%/0% | — | 58.5 | 58.5 | 1.00 | 0 | 1024 | 0.00 | 1.00 |
| 0%/10% | — | 0 | 58.5 | 0 | 1024.00 | 1024 | 1.00 | 1.00 |

The invention claimed is:

1. Antimicrobial composition comprising the L-arginine, $N^\alpha$-lauroyl-ethylester monohydrochloride (LAE) as antimicrobial agent, characterized in that the composition comprises a second component selected from the group consisting of potassium sorbate, calcium sorbate and sorbic acid wherein the composition comprises the components LAE and the second component at a weight ratio of 1:50 to 50:1.

2. The antimicrobial composition according to claim 1 comprising 4% (w/w) of LAE with 10% (w/w) potassium sorbate.

3. The antimicrobial composition according to claim 1 comprising 6% (w/w) of LAE with 8% potassium sorbate.

4. The antimicrobial composition according to claim 1 comprising 1% (w/w) of LAE with 9% (w/w) potassium sorbate.

5. The antimicrobial composition according to claim 1 comprising 7% (w/w) of LAE with 3% (w/w) potassium sorbate.

6. The antimicrobial composition according to claim 1 comprising 9% (w/w) of LAE with 1% (w/w) potassium sorbate.

7. A method for preserving food products comprising adding the antimicrobial agent L-arginine, $N^\alpha$-lauroyl-ethylester monohydrochloride (LAE) and a second component selected from the group consisting of potassium sorbate, calcium sorbate and sorbic acid to the food products wherein the composition comprises the components LAE and the second component at a weight ratio of 1:50 to 50:1.

8. The method for preserving food products according to claim 7 wherein the LAE and second component are added separately from each other.

9. The method for preserving food products according to claim 7 wherein the LAE and second component are combined before being added to the food products.

10. The method for preserving food products according to claim 7 wherein the LAE and second component are added to the food product in a dry form.

11. The method for preserving food products according to claim 10 wherein at least two different ratios of LAE to second component are added in said plurality of steps.

12. The method for preserving food products according to claim 7 wherein the LAE and second component are added to the food products in the form of a solution.

13. The method for preserving food products according to claim 7 wherein the LAE and second component are added as a dispersion.

14. The method for preserving food products according to claim 7 wherein the second component is added in a plurality of steps.

15. The method for preserving food products according to claim 7 wherein said food products are meat, poultry products, fish, crustaceans, vegetables, greens, emulsions, sauces, confectionery, bakery, dairy products, egg-based products, jams, jellies, beverages, juices, wines and beers.

* * * * *